US009562006B2

(12) United States Patent
Fremy

(10) Patent No.: US 9,562,006 B2
(45) Date of Patent: Feb. 7, 2017

(54) PREPARATION OF SYMMETRICAL AND ASYMMETRICAL DISULPHIDES BY REACTIVE DISTILLATION OF MIXTURES OF DISULPHIDES

(71) Applicant: Arkema France, Colombes (FR)

(72) Inventor: Georges Fremy, Sauveterre de Bearn (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/421,344

(22) PCT Filed: Aug. 27, 2013

(86) PCT No.: PCT/FR2013/051974
§ 371 (c)(1),
(2) Date: Feb. 12, 2015

(87) PCT Pub. No.: WO2014/033399
PCT Pub. Date: Mar. 6, 2014

(65) Prior Publication Data
US 2015/0210638 A1 Jul. 30, 2015

(30) Foreign Application Priority Data

Aug. 30, 2012 (FR) ...................... 12 58110

(51) Int. Cl.
| | | |
|---|---|---|
| *C07C 319/24* | (2006.01) | |
| *C07C 319/28* | (2006.01) | |
| *B01J 19/12* | (2006.01) | |

(52) U.S. Cl.
CPC ............ *C07C 319/24* (2013.01); *B01J 19/122* (2013.01); *C07C 319/28* (2013.01); *B01J 2219/1203* (2013.01); *Y02P 20/127* (2015.11)

(58) Field of Classification Search
None
See application file for complete search history.

(56) References Cited

U.S. PATENT DOCUMENTS

| 2,510,893 A | * | 6/1950 | Morton ........................ 546/261 |
|---|---|---|---|
| 2,521,870 A | * | 9/1950 | Proell .............................. 568/21 |
| 2,557,312 A | * | 6/1951 | Proell et al. .................... 568/21 |
| 7,332,145 B2 | | 2/2008 | Chretien |
| 2006/0057056 A1 | | 3/2006 | Chretien |

FOREIGN PATENT DOCUMENTS

| FR | 2875236 | 3/2006 |
|---|---|---|
| WO | 0196499 | 12/2001 |
| WO | 2005111175 | 11/2005 |

OTHER PUBLICATIONS

Birch et al., Journal of the Institute of Petroleum, vol. 39, No. 352, Apr. 1953.*
Mcallan et al., Journal of the American Chemical Society, vol. 73, No. 8, Aug. 6, 1951, pp. 3627-3632.*
Tanaka et al., Tetrahedron Letters 45 (2004) 5677-5679.*
Arisawa et al., Journal of Organometallic Chemistry 691 (2006) 1159-1168.*
International Search Report for International Application No. PCT/FR2013/051974 mailed Dec. 17, 2013.
Birch, S.F., et al., "The preparation and properties of dialkyl di- and poly-sulphides; some disproportionation reactions," Journal of the Institute of Petroleum, vol. 39, No. 352, Apr. 1953, pp. 206-219, XP008162466.
McAllan, D.T., et al., "The preparation and properties of sulfur compounds related to petroleum. I. The dialkyl sulfides and disulfides." Journal of the American Chemical Society, vol. 73, No. 8, Aug. 6, 1951, pp. 3627-3632, XP002055386.
Basu, B., et al., "Merox and related metal phthalocyanine catalyzed oxidation processes," 1993, pp. 571-609, vol. 35, No. 4, Catalysis Reviews: Science Engineering.

* cited by examiner

*Primary Examiner* — Karl J Puttlitz
(74) *Attorney, Agent, or Firm* — RatnerPrestia

(57) ABSTRACT

The invention relates to a process for the preparation of symmetrical or asymmetrical dialkyl disulphides by involving at least one mixture of symmetrical and/or asymmetrical dialkyl disulphides in a basic and/or photochemical catalytic reaction, with joint extraction, preferably continuously, of the symmetrical and/or asymmetrical disulphide(s) which it is desired to obtain.

The process of the invention is particularly suited to the preparation of dimethyl disulphide or diethyl disulphide from a mixture of symmetrical and/or asymmetrical dialkyl disulphides.

12 Claims, 1 Drawing Sheet

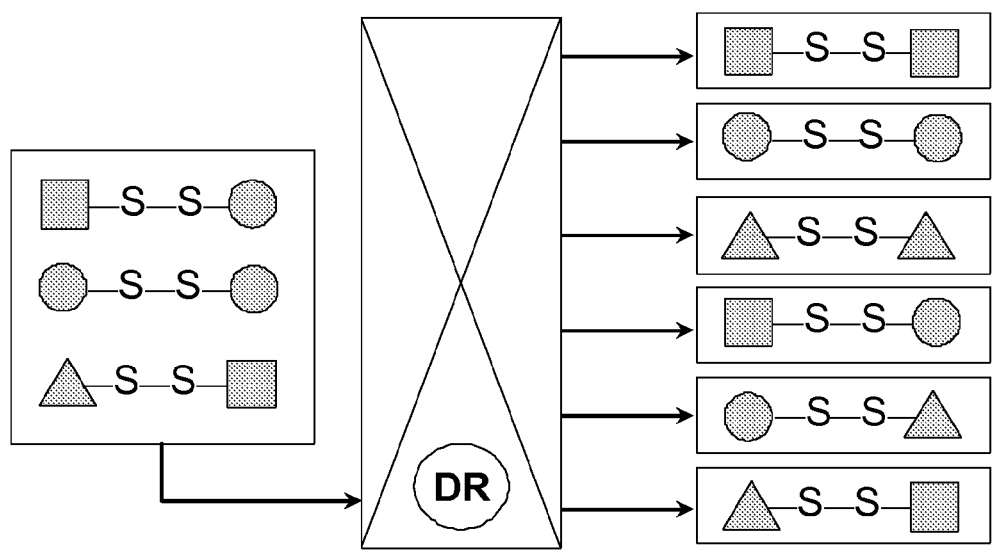

PREPARATION OF SYMMETRICAL AND ASYMMETRICAL DISULPHIDES BY REACTIVE DISTILLATION OF MIXTURES OF DISULPHIDES

CROSS-REFERENCE TO RELATED APPLICATIONS

This is a National Phase filing of International Application No. PCT/FR2013/051974, filed Aug. 27, 2013, which claims priority from French Application No. 12.58110, filed Aug. 30, 2012. The disclosures of both of these applications are incorporated herein by reference in their entirety for all purposes.

FIELD OF THE INVENTION

The present invention relates to a process for the production of symmetrical or asymmetrical dialkyl disulphides by reactive distillation of mixtures of organic disulphides (such as DiSulphide Oils or DSOs). DSOs are mixtures of disulphides originating, for example, from fields for the extraction of gas or oil.

More specifically, the present invention relates to the field of dialkyl disulphides, in particular symmetrical disulphides and more particularly that of dimethyl disulphide and diethyl disulphide.

BACKGROUND OF THE RELATED ART

In the continuation of the present account, dialkyl disulphides and polysulphides are understood to mean the compounds of general formula (1):

$$R-S_n-R' \qquad (1)$$

in which:
R and R', which are identical or different, represent, each independently of one another, a linear or branched hydrocarbon radical comprising from 1 to 12 carbon atoms, preferably from 1 to 8 carbon atoms, and optionally one or more unsaturations in the form of double and/or triple bond(s);
n represents an integer between 2 and 8, preferably between 2 and 6 and more preferably between 2 and 4, limits included.

Dialkyl disulphides are thus represented by the general formula (1) in which n is equal to 2. Dialkyl polysulphides are represented by the general formula (1) in which n is strictly greater than 2.

The dialkyl disulphides and polysulphides of formula (1) are said to be symmetrical when the R and R' radicals are identical and are said to be asymmetrical when R and R' are different. "Identical" is understood to mean having the same number of carbon atoms and having the same stereochemical configuration. In the context of the present invention, preference is given to dialkyl disulphides of above formula (1) (where n=2) for which R and R', which are identical or different, represent a linear or branched hydrocarbon chain which comprises from 1 to 12 carbon atoms, preferably from 1 to 8 carbon atoms, and which is saturated (alkyl radical).

Preference is given, among the alkyl radicals which can form the R and R' radicals, to radicals comprising from 1 to 8 carbon atoms, preferably from 1 to 6 carbon atoms, for example the methyl, ethyl, n-propyl, isopropyl, n-butyl, isobutyl, tert-butyl, n-pentyl, neopentyl and n-hexyl radicals.

In the context of the present invention, preference is given to the dialkyl disulphides chosen from dimethyl disulphide (or DMDS), diethyl disulphide (or DEDS), dipropyl disulphide (or DPDS), dibutyl disulphide (or DBDS), dipentyl disulphide (or diamyl disulphide) or dihexyl disulphide, the trisulphide homologues (n=3), tetrasulphide homologues (n=4), pentasulphide homologues (n=5) or hexasulphide homologues (n=6) of these disulphides, and their mixtures, it being understood that the propyl and butyl radicals can exist in the linear or branched form, for example n-propyl, isopropyl, n-butyl, isobutyl, sec-butyl and tert-butyl, n-pentyl, sec-pentyl, neopentyl and others.

Among the dialkyl disulphides, dimethyl disulphide (DMDS) is a compound very widely used today in a great many industrial fields, for example chemical industries, petrochemical industries, in agrochemistry, in the building industry, and others. DMDS is used in particular as agent for the sulphurization of catalysts for the hydrotreating of petroleum feedstocks or as feedstock additive for steam cracking.

In comparison with other products used in these applications, such as commercial tert-alkyl polysulphides, DMDS exhibits numerous advantages, in particular a high sulphur content (68%) and non-coking decomposition products ($CH_4$, $H_2S$). Furthermore, in these applications, DMDS results in performances which are generally superior to those of other products, such as tert-alkyl polysulphides.

Among methods for the synthesis of DMDS, a particularly effective and economical method is the oxidation of methyl mercaptan by sulphur according to the reaction:

$$2CH_3SH + S \xrightarrow{\text{catalyst}} CH_3SSCH_3 + H_2S$$

This reaction is catalysed by organic or inorganic and homogeneous or heterogeneous basic agents. This route is particularly economical when it is considered that $H_2S$ is coproduced and that the latter can be used to carry out the synthesis of methyl mercaptan by reaction with methanol according to the following reaction:

$$CH_3OH + H_2S \xrightarrow{\text{catalyst}} CH_3SH + H_2O$$

There exist other routes for the synthesis of DMDS described in the prior art, such as the oxidation of methyl mercaptan by aqueous hydrogen peroxide solution or atmospheric oxygen.

There has now been found another route for the production of DMDS and more generally of symmetrical or asymmetrical dialkyl disulphides, this other synthetic route exhibiting an economic advantage at least equivalent to that introduced by the process of the oxidation of methyl mercaptan by sulphur and in addition exhibiting the great advantage of making possible an entirely advantageous recovery in value of DSOs.

DSOs (DiSulphide Oils) are mixtures of organic disulphides produced during the treatment of the mercaptans present in petroleum fractions or gases liquefied by processes of "Merox" type (see, for example, *Catal. Review—Sci. Eng.*, 35(4), (1993), 571-609).

These DSOs are generally and most often removed, destroyed or stored, according to different techniques, on the very site of production, in particular on gas sites, for example in sulphur recovery units. One of the techniques for destroying DSOs commonly used is that based on the Claus reaction, which makes possible a joint removal of the hydrogen sulphide ($H_2S$) also present in crude natural gas.

The Claus reaction can be written according to the following reaction (A):

$$2H_2S + SO_2 \rightarrow 3S + 2H_2O, \quad (A)$$

the sulphur dioxide ($SO_2$) being prepared by oxidation of a portion of the $H_2S$, according to the following reaction (B):

$$H_2S + 3/2 O_2 \rightarrow SO_2 + H_2O \quad (B)$$

and also by oxidizing treatment of the DSOs, according to the following reaction (C), where the DSOs are illustrated by DMDS:

$$CH_3SSCH_3 + 11/2 O_2 \rightarrow 2CO_2 + 2SO_2 + 3H_2O. \quad (C)$$

The problem is that the reactions (A) and (B) are carried out with a shortage of oxygen, whereas the reaction (C) requires an excess of oxygen, with respect to the stoichiometry, in order to be complete as the presence of unburnt carbon-based residues in the Claus reaction causes serious problems of quality of the sulphur obtained by this reaction. The amount of DSOs which it is thus possible to treat in conjunction with the $H_2S$ incineration is very limited and often less than the amount produced daily on the gas site concerned.

Patent Application FR 2 875 236 A describes very well the problems encountered with this removal technique and its alternative forms. This patent application also provides another destruction method based on the complete hydrogenolysis of these disulphides to give hydrocarbons and $H_2S$, followed by incineration of the latter in a Claus unit.

With the aim of recovering in value rather than destroying the DSOs, International Application WO 2005/111175 provides for the use of these products as inhibitors of the formation of coke in hydrocarbon cracking furnaces. This is because it is known by a person skilled in the art that the addition of sulphur-comprising compounds (such as, for example, DMDS) to hydrocarbon feedstocks makes it possible to greatly reduce the formation of coke in the pipes of steam crackers, for example.

However, as is mentioned in International Application WO 2001/96499, DSOs are formed by oxidation of the sodium salts of the mercaptans to be removed and for this reason comprise traces of sodium in a significant amount. This has the consequence of the impossibility of a direct use, without pretreatment, in cracking furnaces as the presence of sodium modifies the metallurgy of the cracking pipes. Furthermore, the use of DSOs in another application, such as the sulphurization of catalysts for the hydrotreating of petroleum fractions, is also compromised as sodium is known to be a poison for these catalysts.

The direct recovery in value of these DSOs as synthetic intermediates is also impeded by the fact, this time, that these DSOs are mixtures of disulphides and not chemically pure molecules, such as dimethyl disulphide or diethyl disulphide, taken in isolation. For example, a DSO resulting from the treatment of a liquefied petroleum gas (LPG) comprises dimethyl disulphide, diethyl disulphide and a significant amount of ethyl methyl disulphide.

Other processes relate more specifically to symmetrical and asymmetrical disulphides. Thus, U.S. Pat. No. 2,521,870 discloses a process which makes it possible to prepare asymmetrical disulphides from a mixture of at least two different symmetrical disulphides ("disproportionation"), by heating in the presence of sodium salts. It is also known, from U.S. Pat. No. 2,557,312, to prepare symmetrical disulphides from asymmetrical disulphides ("reproportionation") starting from a mixture of at least two asymmetrical disulphides by heating in the presence of an alkanolamine and of an alkali metal sulphide.

Furthermore, an obvious solution for a person skilled in the art desirous of producing pure, symmetrical and unmixed dialkyl disulphides from DSOs would consist in separating the various dialkyl disulphides by a distillation as a function of the boiling points. However, this technique would not make it possible to recover in value the asymmetrical dialkyl disulphides as symmetrical dialkyl disulphides, such as the ethyl methyl disulphide present in the DSOs resulting from LPG, this asymmetrical disulphide even sometimes being the predominant compound.

It is the same for more complex DSOs (complex mixtures of dialkyl disulphides resulting from condensates, for example) in which disulphides having alkyl groups of lower ranks, such as $C_1$, $C_2$, $C_3$ or $C_4$ alkyl groups, indeed even of higher ranks, are present. In these DSOs, symmetrical disulphides can be in relatively low amounts, in comparison with the asymmetrical disulphides, in the light of the various possible combinations ($C_1/C_2$, $C_1/C_3$, $C_1/C_4$, $C_2/C_3$, and the like) and the possibility of structural isomers starting from the $C_3$ rank (isopropyl/n-propyl).

SUMMARY OF THE INVENTION

Thus, in addition to the first objective of providing a particularly economic alternative form of the specific process for the preparation of DMDS, another objective of the present invention is to provide, more generally, a process for the recovery in value of DSOs. Yet another objective of the present invention consists in recovering and producing, advantageously, pure, unmixed, symmetrical or asymmetrical, dialkyl disulphides with an improved yield, indeed even a maximum yield. Yet other objectives will become apparent in the account of the invention which follows.

It has now been discovered that it is possible to achieve these objectives, at least in part, indeed even in totality, by virtue of the process of the present invention.

Thus, and according to a first aspect, the invention relates to a process for the preparation of symmetrical or asymmetrical dialkyl disulphides by involving at least one DSO in a basic and/or photochemical catalytic reaction, with joint extraction, preferably continuously, of the symmetrical and/or asymmetrical disulphide(s) which it is desired to obtain.

More specifically, the process of the invention relates to a process for the preparation of symmetrical or asymmetrical dialkyl disulphides, the said process comprising at least the following stages:

a) introduction, into a reactor, of at least one mixture of at least two organic disulphides of general formula (1):
  R—$S_n$—R', in which:
  R and R', which are identical or different, represent, each independently of one another, a linear or branched hydrocarbon radical comprising from 1 to 12 carbon atoms, preferably from 1 to 8 carbon atoms, and optionally one or more unsaturations in the form of double and/or triple bond(s); and
  n represents 2, b) carrying out a basic and/or photochemical catalytic reaction, during which the compounds of formula (1) are converted, by reproportionation and by disproportionation, into a mixture of symmetrical and/or asymmetrical dialkyl disulphides, c) extraction, preferably continuously, of the symmetrical and/or asymmetrical dialkyl disulphide(s) desired.

DETAILED DESCRIPTION OF THE INVENTION

In the process according to the present invention, the basic catalyst can be of any type known to a person skilled in the art, for example a homogeneous or heterogeneous and supported or non-supported catalyst, for example a basic catalyst chosen from amines, alkali metal or alkaline earth metal hydroxides, such as, for example, sodium hydroxide, metal oxides, such as magnesium oxide (MgO), anion-exchange resins, and others and their mixtures. It should be understood that the said basic catalyst makes it possible to catalyse both the disproportionation reactions and the reproportionation reactions.

It is possible to use, as solid basic catalyst appropriate for a heterogeneous basis catalysis, any type of solid and basic catalyst known to a person skilled in the art and in particular catalysts having a solid support which is generally impregnated with at least one alkali metal or alkaline earth metal oxide or with a metal oxide, such as, for example, $Na_2O$, $K_2O$, MgO, CaO, and others, and their mixtures. Mention may be made, among the solid supports, as nonlimiting examples, of porous supports known to a person skilled in the art, such as alumina, silica, zeolites, charcoals, active charcoals, clays, zirconias, titanium dioxide, and others, but also ion-exchange polymer resins, preferably anion-exchange polymer resins, which are weakly or strongly basic, such as, for example, Amberlyst® A21 from Dow Chemicals.

A catalyst entirely suited to the process of the invention, according to the heterogeneous basic catalysis mode, is sodium oxide ($Na_2O$) supported on alumina, and sold by Axens under the name CM2-5.

According to an alternative form, the catalytic reaction of the process of the present invention can be a photochemical reaction. It should also be understood that this photochemical reaction makes it possible to catalyse both the disproportionation reactions and the reproportionation reactions.

Use is generally made, in this case, of a source of radiation within the ultraviolet range, between approximately 260 nm and approximately 350 nm. A lamp very particularly suited to the photochemical catalysis reaction of the process of the present invention is an ultraviolet lamp having a wavelength of 265 nm, which makes possible direct and rapid photolysis of the disulphides, even without the help of photoinitiators, which generate generally slower reactions.

The catalytic reaction of the process of the invention can combine a homogeneous or heterogeneous basic catalysis, with a supported or non-supported catalyst, and a photochemical catalysis. The basic and/or photochemical catalysis reaction (stage b)) can be carried out at any appropriate temperature adjusted according to the knowledge of a person skilled in the art. For example, the temperatures adjusted for carrying out the reaction according to the process of the present invention can be between approximately −10° C. and +300° C., preferably between +20° C. and +200° C.

The reaction pressure can also vary within wide proportions, according in particular to the reaction temperature, the reactants and the products desired, and can vary from 1 mbar (medium vacuum) to several tens of bars, for example from 10 mbar (slight vacuum) to approximately 3 bar. According to a preferred embodiment, the process of the present invention is carried out at atmospheric pressure, or under slight vacuum or under medium vacuum.

The process according to the invention thus makes it possible to obtain, starting from mixtures of symmetrical and/or asymmetrical disulphides, such as, for example, those present in DSOs, in a simple and rapid way and with good yields, symmetrical and/or asymmetrical disulphides of high purity.

In the reaction medium, and after carrying out the catalytic reaction, the symmetrical and/or asymmetrical disulphides formed are the reproportionation and disproportionation products of the starting disulphides and, consequently, the said reaction medium comprises, in addition to the starting materials, other symmetrical and/or asymmetrical disulphides.

The following scheme illustrates one of the possible reactions, in which an asymmetrical disulphide results in two symmetrical disulphides (reproportionation) and vice-versa (disproportionation), according to the following reaction (D):

$2CH_3SSCH_2CH_3(EMDS) \rightleftharpoons CH_3SSCH_3$
$(DMDS)+CH_3CH_2SSCH_2CH_3(DEDS)$ This reaction is an equilibrium reaction and the equilibrium can be displaced by extraction, preferably continuously, of one or more products which it is desired to obtain.

On taking up again the above scheme, another example consists in using a mixture of EMDS (asymmetrical disulphide) and of dibutyl disulphide (DBDS, symmetrical disulphide). According to the process of the invention, the reaction scheme can thus be written:

EMDS+DBDS $\rightleftharpoons$ DMDS+DEDS+EBDS+ MBDS+DBDS in which scheme EBDS is ethyl butyl disulphide, MBDS is methyl butyl disulphide and DBDS is dibutyl disulphide. This example shows that, starting from a mixture of two disulphides, it is possible to obtain four other disulphides.

FIG. 1 gives a diagrammatic representation of the disulphides which can be formed, in the RD reactor (which illustrates a reactive distillation column), from a mixture of three disulphides (two symmetrical disulphides and one asymmetrical disulphide), in which the symbols ■, • and ▲ each represent an alkyl radical chosen from R and R' defined above. The catalytic and/or photochemical disproportionation and reproportionation reactions described above are all equilibrium reactions, and the symmetrical or asymmetrical disulphide or disulphides of interest can be easily extracted from the reaction medium, this having the well known effect of displacing the reaction equilibrium.

The extraction (stage c)) of the symmetrical or asymmetrical disulphide or disulphides of interest can be carried out according to any method or any combination of methods known to a person skilled in the art, among which may be mentioned, for example, withdrawal or distillation, these two methods being preferred, separately or in combination. Thus, and according to a very particularly preferred embodiment, the process of the present invention can be carried out in a column of distillation column type, comprising the basic catalyst and/or provided with equipment which makes possible photocatalysis.

Thus, the disproportionation and reproportionation reactor makes possible, at the same time, the extraction of the symmetrical or asymmetrical disulphide or disulphides of interest by simple distillation. Thus, as the reactions are equilibrium reactions, as indicated above, the boiler of the distillation or the column bottom becomes gradually enriched in the least volatile disulphide (for example DEDS, in the above reaction (D)), whereas the distillation top becomes enriched in the most volatile disulphide (DMDS, in the above reaction (D)).

The distillation technique is a technique well known to a person skilled in the art and can be carried out in a distillation column, batchwise or continuously. It is preferable to carry out the extraction of the desired product or products in a distillation column, for example under the conditions described in U.S. Pat. No. 2,557,312, according to the nature of the disulphides or of the mixtures of disulphides present, and also according to the nature of the products which it is desired to obtain. The distillation operation can thus be carried out under atmospheric pressure, preferably under slight or medium vacuum, so as to avoid distillation temperatures greater than approximately 200° C.

Typically, the process of the present invention comprises a catalytic reaction stage of disproportionation and/or of reproportionation, together with a stage of extraction, preferably by distillation, of the desired reaction product or products, making it possible to shift the equilibrium of the said catalytic reaction. This process can thus be defined as a "reactive distillation" of dialkyl disulphide(s).

According to a preferred embodiment of the process of the invention, the mixture of disulphides, for example a mixture of DSO, after treatment by basic catalysis, preferably heterogeneous basic catalysis, and/or photochemical catalysis, is distilled in order to displace the equilibrium represented in the above reactions towards the right, as the lightest symmetrical or asymmetrical dialkyl disulphide or disulphides is/are withdrawn, the heaviest symmetrical dialkyl disulphide or disulphides remaining in the boiler or in the column bottom.

In the reactive distillation mode set out above, the lightest product or products, extracted in the gaseous form, are liquefied according to conventional techniques known to a person skilled in the art, for example by cooling.

The heaviest compounds remaining in the boiler can also be separated by increasing the temperature and/or decreasing the pressure, in order to continue the separation of the said compounds. The heaviest compound remaining in the boiler is thus obtained in the pure form, contrary to what may be obtained by employing the processes described in the prior art.

The process of the present invention can be carried out batchwise or continuously. It is preferable to carry out the process of the invention batchwise when it is a matter of treating a batch of mixtures of disulphides which can be charged in one go to the reactor, and it is preferable to carry out the process of the invention continuously when the reactor is fed continuously with a stream of mixture of disulphides originating from an extraction site which generates such mixtures, for example the mixtures of disulphides (DSOs) produced during the treatment of the mercaptans present in petroleum fractions or gases liquefied by processes of "Merox" type.

It is possible to carry out first of all the catalytic reaction (basic and/or photochemical catalytic reaction, as indicated above) and then the extraction of the symmetrical or asymmetrical disulphide or disulphides of interest, or else to combine the catalytic reaction (basic and/or photochemical catalytic reaction, as indicated above) and the extraction of the symmetrical or asymmetrical disulphide or disulphides of interest, this alternative form being very particularly preferred. In this case, the process of the invention is carried out in a "reactive distillation" column, combining the reproportionation and/or disproportionation reactions and also the extraction by distillation of the symmetrical or asymmetrical disulphide or disulphides of interest.

In an embodiment very particularly suited to the process of the present invention, the reactive distillation is carried out continuously, which offers the advantage of obtaining dialkyl disulphides, for example symmetrical dialkyl disulphides, for example DMDS, which are pure (since already distilled) and which can be used directly.

Another advantage of the process of the present invention lies in the fact that the dialkyl disulphides thus obtained directly by reactive distillation of DSOs are freed from the inorganic and organic impurities present in the DSOs.

By virtue of the process of the present invention, the yields of pure dialkyl disulphides obtained are greater than those which would have been obtained with a simple distillation of the DSOs, the said process of the invention making it possible to convert the great majority, indeed even all, of the asymmetrical disulphides into symmetrical disulphides.

According to an advantageous alternative form of the process according to the present invention, the catalytic reaction can be carried out directly in the distillation column. One embodiment of this preferred alternative form comprises a bed of basic catalyst incorporated in a distillation column.

The process of the present invention is very particularly suited to the preparation of "pure" symmetrical dialkyl disulphides from DSOs but can also be applied to the preparation of "pure" asymmetrical dialkyl disulphides from DSOs by carrying out a specific distillation, by displacing the stoichiometry (withdrawal/extraction of the symmetrical or asymmetrical disulphide or disulphides of interest) with an appropriate apparatus.

Thus, the present invention provides a process very particularly suited to the recovery in value of the DSOs by reactive distillation to result, in a reactive distillation stage, in one or more symmetrical and/or asymmetrical dialkyl disulphides which are pure and which can be used directly, without requiring an additional purification operation.

According to a very particularly preferred aspect of the present invention, the process described above makes possible, as nonlimiting example, the preparation of dimethyl disulphide (DMDS); more specifically, the process of the present invention relates to the synthesis of DMDS by reactive distillation starting from a DSO, the distillation being carried out at atmospheric pressure and the temperature of the boiler being approximately 110° C.-150° C., for example 130° C. The DMDS is then withdrawn at the column top at its boiling point, which is 109° C. at atmospheric pressure.

According to another aspect, the process of the present invention makes possible the preparation of diethyl disulphide; more specifically, the process of the present invention relates to the synthesis of DEDS by reactive distillation from a DSO, the distillation being carried out at atmospheric pressure and the temperature of the boiler being approximately 160-180° C., for example 170° C. The DEDS is then withdrawn in its turn at the column top at its boiling point, which is 154° C. at atmospheric pressure.

A better understanding of the invention will be obtained with the following examples:

Example 1: (Comparative)

Take 152 g of mixture of disulphides comprising 89.4 g of DMDS (dimethyl disulphide), 55.1 g of EMDS (ethyl methyl disulphide) and 7.5 g of DEDS (diethyl disulphide).

The distillation of this mixture, in the absence of basic or photochemical catalysis, results in the recovery of 88.5 g of DMDS, i.e. 99% of the amount initially present.

Example 2

Take 152 g of the mixture of Example 1 to which 2% of a 50% by weight aqueous sodium hydroxide solution are added. The combined mixture is used in a reactive distillation according to the present invention.

The DMDS is continuously withdrawn at the column top and is liquefied by cooling according to conventional techniques known to a person skilled in the art. The amount of DMDS recovered after distillation is 98.3 g and represents 110% of the amount initially present.

Example 3

Take 321.5 g of another DSO, a mixture initially relatively poor in DMDS (DMDS 5% by weight, EMDS 34.5% and DEDS 60.5%). Expressed by weight, this mixture thus comprises 16.1 g of DMDS, 110.9 g of EMDS and 194.5 g of DEDS. The reactive distillation according to the present invention is carried out in the presence of 50 g of an alumina doped with 3% of $Na_2O$ (CM 2-5 catalyst from Axens).

The amount of DMDS recovered after distillation is 63 g and represents 390% of the amount initially present.

The analysis of the contents of the boiler shows that it comprises 255.2 g of DEDS and 3.3 g of EMDS. The degree of conversion of the EMDS (asymmetrical) is thus 97%.

The invention claimed is:

1. A process for preparing symmetrical or asymmetrical dialkyl disulphides, the process comprising at least the following stages:
    a) introducing, into a reactor, at least one mixture of at least two organic disulphides of general formula (1):
    R—$S_n$—R', in which:
        R and R', which are identical or different, represent, each independently of one another, a linear or branched hydrocarbon radical comprising from 1 to 12 carbon atoms, and optionally one or more unsaturations in the form of double and/or triple bond(s); and
        n represents 2,
    b) carrying out a basic catalytic reaction or a basic and photochemical catalytic reaction, wherein a basic catalyst is used which is a supported catalyst and/or a heterogeneous catalyst, during which the organic disulphides of formula (1) are converted, by reproportionation and by disproportionation, into a mixture of symmetrical and/or asymmetrical dialkyl disulphides,
    c) extracting the symmetrical and/or asymmetrical dialkyl disulphide(s) desired.

2. The process according to claim 1, wherein a catalyst is used in stage b) which is a photocatalyst for radiation of between approximately 260 nm and approximately 350 nm.

3. The process according to claim 1, wherein stage b) is carried out at a temperature of between approximately −10° C. and +300° C.

4. The process according to claim 1, wherein the extraction stage c) comprises withdrawal or distillation or a combination of these two techniques.

5. The process according to claim 1, wherein the process is carried out in a column of distillation column type, comprising a basic catalyst and optionally provided with equipment which makes possible photocatalysis.

6. The process according to claim 1, wherein the process is carried out batchwise or continuously.

7. The process according to claim 1, wherein dimethyl disulphide is prepared.

8. The process according to claim 1, wherein diethyl disulphide is prepared.

9. The process according to claim 1, wherein stage c) is carried out continuously.

10. The process according to claim 1, wherein R and R' represent, each independently of one another, a linear or branched hydrocarbon radical comprising from 1 to 8 carbon atoms.

11. The process according to claim 1, wherein the basic catalyst is a supported catalyst comprising a solid support and the solid support is an anion-exchange polymer resin.

12. The process according to claim 1, wherein the basic catalyst is a catalyst on a solid support impregnated with at least one alkali metal or alkaline earth metal oxide or with a metal oxide, the solid support being selected from the group consisting of alumina, silica, zeolites, charcoals, active charcoals, clays, zirconias, titanium dioxide and ion-exchange polymer resins which are weakly or strongly basic.

* * * * *